US010695069B2

(12) United States Patent
Guerrera et al.

(10) Patent No.: US 10,695,069 B2
(45) Date of Patent: Jun. 30, 2020

(54) CIRCULAR STAPLING DEVICE WITH OFFSET SPLINE TIP

(71) Applicant: Covidien LP, Mansfield, MA (US)

(72) Inventors: Joseph Guerrera, Watertown, CT (US); Charles Kollar, West Hartford, CT (US)

(73) Assignee: Covidien LP, Mansfield, MA (US)

( * ) Notice: Subject to any disclaimer, the term of this patent is extended or adjusted under 35 U.S.C. 154(b) by 190 days.

(21) Appl. No.: 16/037,532

(22) Filed: Jul. 17, 2018

(65) Prior Publication Data

US 2019/0059901 A1   Feb. 28, 2019

Related U.S. Application Data

(60) Provisional application No. 62/549,266, filed on Aug. 23, 2017.

(51) Int. Cl.
*A61B 17/115* (2006.01)
*A61B 17/00* (2006.01)
*A61B 90/00* (2016.01)
*A61B 17/072* (2006.01)

(52) U.S. Cl.
CPC .... *A61B 17/1155* (2013.01); *A61B 17/00234* (2013.01); *A61B 2017/00367* (2013.01); *A61B 2017/00473* (2013.01); *A61B 2017/00477* (2013.01); *A61B 2017/07257* (2013.01); *A61B 2017/07271* (2013.01); *A61B 2090/0811* (2016.02)

(58) Field of Classification Search
USPC ....................................................... 227/179.1
See application file for complete search history.

(56) References Cited

U.S. PATENT DOCUMENTS

| | | | |
|---|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |

(Continued)

FOREIGN PATENT DOCUMENTS

| CA | 908529 A | 8/1972 |
|---|---|---|
| CA | 2805365 A1 | 8/2013 |

(Continued)

OTHER PUBLICATIONS

European Search Report dated Jan. 30, 2019, issued in EP Appln. No. 18190300.

*Primary Examiner* — Michelle Lopez
*Assistant Examiner* — Chinyere J Rushing-Tucker
(74) *Attorney, Agent, or Firm* — Carter, DeLuca & Farrell LLP

(57) ABSTRACT

A surgical stapling device includes an anvil assembly and a shell assembly. The anvil and shell assemblies each include splines that define guide channels. Each of the anvil splines defines a distally positioned triangular tip that is defined by an apex and first and second right cam surfaces. The cam surfaces of the anvil splines are configured to engage one of the shell splines to cam or rotate the anvil assembly into alignment with the shell assembly as the anvil assembly is moved in relation to the shell assembly to a clamped position.

20 Claims, 11 Drawing Sheets

(56) References Cited

U.S. PATENT DOCUMENTS

| | | |
|---|---|---|
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |

(56) References Cited

U.S. PATENT DOCUMENTS

| | | |
|---|---|---|
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |

(56) References Cited

U.S. PATENT DOCUMENTS

| | | |
|---|---|---|
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |

(56) References Cited

U.S. PATENT DOCUMENTS

| | | |
|---|---|---|
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3108825 A2 | 12/2016 |
| EP | 3366234 A1 | 8/2018 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

CIRCULAR STAPLING DEVICE WITH OFFSET SPLINE TIP

CROSS-REFERENCE TO RELATED APPLICATIONS

This application claims the benefit of and priority to U.S. Provisional Patent Application Ser. No. 62/549,266 filed Aug. 23, 2017, the entire disclosure of which is incorporated by reference herein.

BACKGROUND

1. Technical Description

The present disclosure is directed to circular stapling devices, and more particularly, to circular stapling devices including splines having offset spline tips configured to prevent malformation of staples due to spline crashing.

2. Background of Related Art

Circular stapling devices are utilized by clinicians to apply one or more surgical fasteners, e.g., staples or two-part fasteners, to body tissue for the purpose of joining segments of body tissue together and/or for the creation of an anastomosis. Circular stapling devices generally include a shell assembly including a staple cartridge supporting a plurality of annular rows of staples and an anvil assembly operatively associated with the shell assembly and having annular arrays of staple receiving pockets. The staple receiving pockets are aligned with the annular rows of staples to provide a surface against which the plurality of annular rows of staples can be formed.

During a typical tissue fastening procedure, the anvil assembly of the stapling device is positioned within one segment of body tissue and the shell assembly is positioned in an adjacent segment of body tissue. The anvil assembly is then attached to the body portion of the stapling device and the stapling device is actuated to move the anvil assembly in relation to the staple cartridge of the shell assembly to clamp the body tissue segments together.

Typically, the anvil assembly includes an anvil shaft that includes splines that mate with splines formed within a shell housing of the shell assembly to align the staple forming pockets of the anvil assembly with staple receiving pockets of the staple cartridge of the shell assembly. The splines on the anvil shaft and on the shell housing of the shell assembly include first and second tapered ends that define an apex. When the tapered ends of the splines of the anvil assembly engage the tapered ends of the shell assembly, the anvil assembly is cammed into rotation to align the staple forming pockets of the anvil assembly with staple receiving pockets of the staple cartridge of the shell assembly. However, if the apexes of the splines of the anvil assembly and the shell assembly engage head on, i.e., crash, the splines of the anvil assembly and the shell assembly may be damaged such that proper alignment of the anvil and shell assemblies is prevented such that malformation of the staples may occur during firing of the stapling device.

A continuing need exists for a circular stapling device having a more reliable alignment structure for aligning the staple forming pockets of the anvil assembly with the staple receiving pockets of the staple cartridge of the shell assembly to minimize the occurrence of staple malformation.

SUMMARY

One aspect of the disclosure is directed to a surgical stapling device including an approximation assembly, a shell assembly, and an anvil assembly. The approximation assembly includes an anvil retainer. The shell assembly includes a staple cartridge and a shell housing having an inner housing portion defining a bore. The inner housing portion supports a plurality of shell splines positioned within the bore. Each of the plurality of shell splines defines a guide channel with an adjacent one of the plurality of shell splines. The staple cartridge is supported on the shell housing. The anvil assembly includes an anvil shaft having at least one anvil spline and an anvil head having an anvil surface defining a plurality of staple deforming recesses. The at least one anvil spline defines a longitudinal axis. The anvil shaft is configured to releasably engage the anvil retainer and the anvil head is supported on a distal portion of the anvil shaft. The at least one anvil spline includes first and second tapered surfaces that intersect at an apex that is offset to one side of the longitudinal axis. The first tapered surface has a surface area $\beta$ and the second tapered surface has a surface area $\Omega$ that is different from surface area $\beta$.

Another aspect of the present disclosure is directed to an anvil assembly for a circular stapling device including an anvil shaft having at least one anvil spline and an anvil head having an anvil surface defining a plurality of staple deforming recesses. The at least one anvil spline defines a longitudinal axis. The anvil head is supported on a distal portion of the anvil shaft. The at least one anvil spline includes first and second tapered surfaces that intersect at an apex that is offset to one side of the longitudinal axis. The first tapered surface has a surface area $\beta$ and the second tapered surface has a surface area $\Omega$ that is different from surface area $\beta$.

Another aspect of the disclosure is directed to a tool assembly including a shell assembly and an anvil assembly. The shell assembly includes a staple cartridge and a shell housing. The shell housing has an inner housing portion defining a bore and a plurality of shell splines supported on the inner housing portion within the bore. Each of the plurality of shell splines defines a guide channel with an adjacent one of the plurality of shell splines. The staple cartridge is supported on the shell housing. The anvil assembly includes an anvil shaft having at least one anvil spline and an anvil head having an anvil surface defining a plurality of staple deforming recesses. The at least one anvil spline defines a longitudinal axis. The anvil head is supported on a distal portion of the anvil shaft. The at least one anvil spline includes first and second tapered surfaces that intersect at an apex that is offset to one side of the longitudinal axis. The first tapered surface has a surface area $\beta$ and the second tapered surface has a surface area $\Omega$ that is different from surface area $\beta$.

In embodiments, $\beta$ is at least 1.5 times greater than $\Omega$.

In some embodiments, $\beta$ is at least 2 times greater than $\Omega$.

In certain embodiments, the at least one anvil spline is formed from metal and the plurality of shell splines is formed from a polymer.

In embodiments, each of the plurality of shell splines defines a longitudinal axis and includes first and second tapered cam surfaces. The first and second tapered cam surfaces of each of the plurality of shell splines intersect at an apex.

In some embodiments, the apex of each of the plurality of shell splines is aligned with the longitudinal axis of the shell spline.

In certain embodiments, the first cam surface of each of the plurality of shell splines has a surface area that is equal to a surface area of the second cam surface of each of the plurality of shell splines.

In embodiments, at least one the anvil spline is formed to migrate into a respective shell spline of the plurality of the shell splines when the apex of the at least one anvil spline engages the apex of a respective one of the plurality of shell splines.

BRIEF DESCRIPTION OF THE DRAWINGS

Various embodiments of the presently disclosed circular stapling device are described herein below with reference to the drawings, wherein.

DETAILED DESCRIPTION OF EMBODIMENTS

Figure 1:
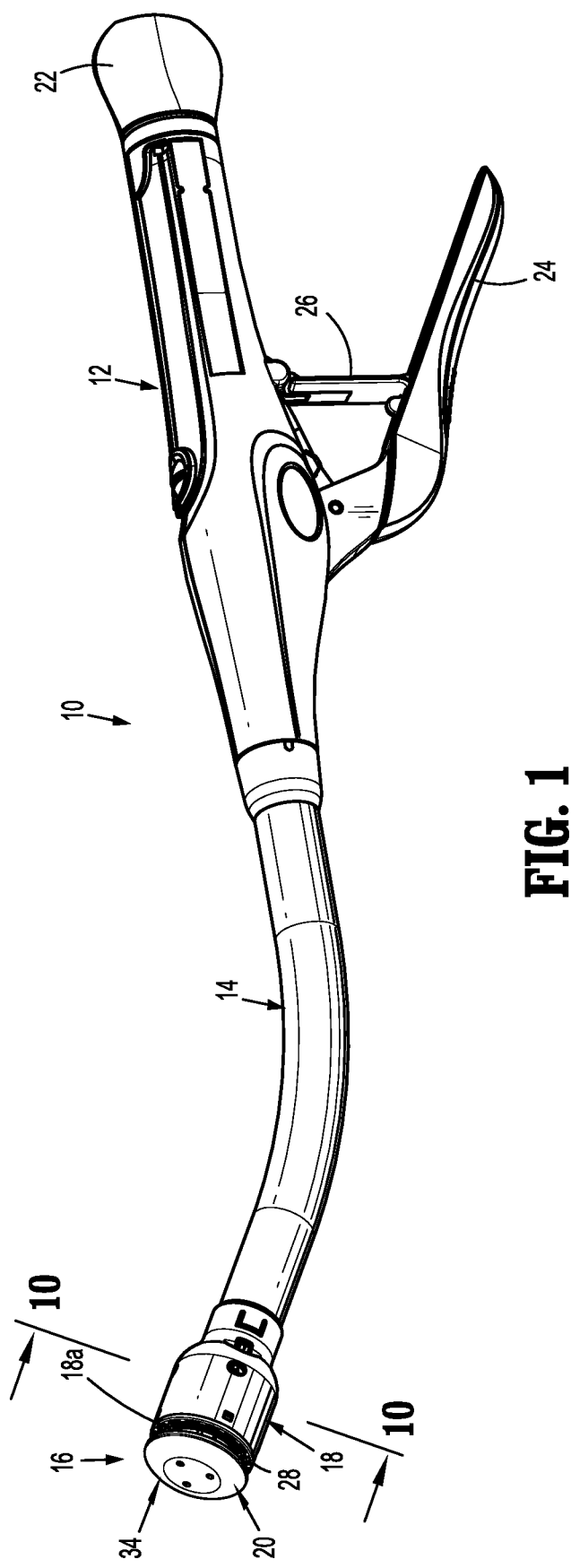
FIG. 1 is a side perspective view of an exemplary embodiment of the presently disclosed circular stapling device with a tool assembly in a clamped position.

The presently disclosed circular stapling device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

The presently disclosed surgical stapling device includes an anvil assembly and a shell assembly. The anvil and shell assemblies each include splines that define guide channels. The guide channels defined by the shell splines receive the anvil splines to properly align the anvil assembly with the shell assembly. Each of the shell splines defines a distally positioned triangular tip that is defined by an apex and first and second cam surfaces. The first and second cam surfaces of each shell spline are configured to engage one of the anvil splines to cam or rotate the anvil assembly into alignment with the shell assembly. Similarly, each of the anvil splines defines a proximally positioned triangular tip that is defined by an apex and first and second cam surfaces. The cam surfaces of the anvil splines are also configured to engage one of the shell splines to cam or rotate the anvil assembly into alignment with the shell assembly. The apex of each of the anvil splines is offset from a longitudinal axis of the anvil spline such that the first and second cam surfaces of the anvil splines have different surface areas. By providing anvil splines that have cam surfaces with a different surface areas, a greater force is applied to the cam surface of the anvil spline having the greater surface area when the splines of the anvil assembly and the shell assembly crash. As such, when crashing of the splines occurs the anvil splines will be pushed in one direction to rotate the anvil assembly in relation to the shell assembly out of the crashed position to direct the anvil splines into the guide channels defined by the shell splines to properly align the shell assembly with the anvil assembly.

Figure 2:
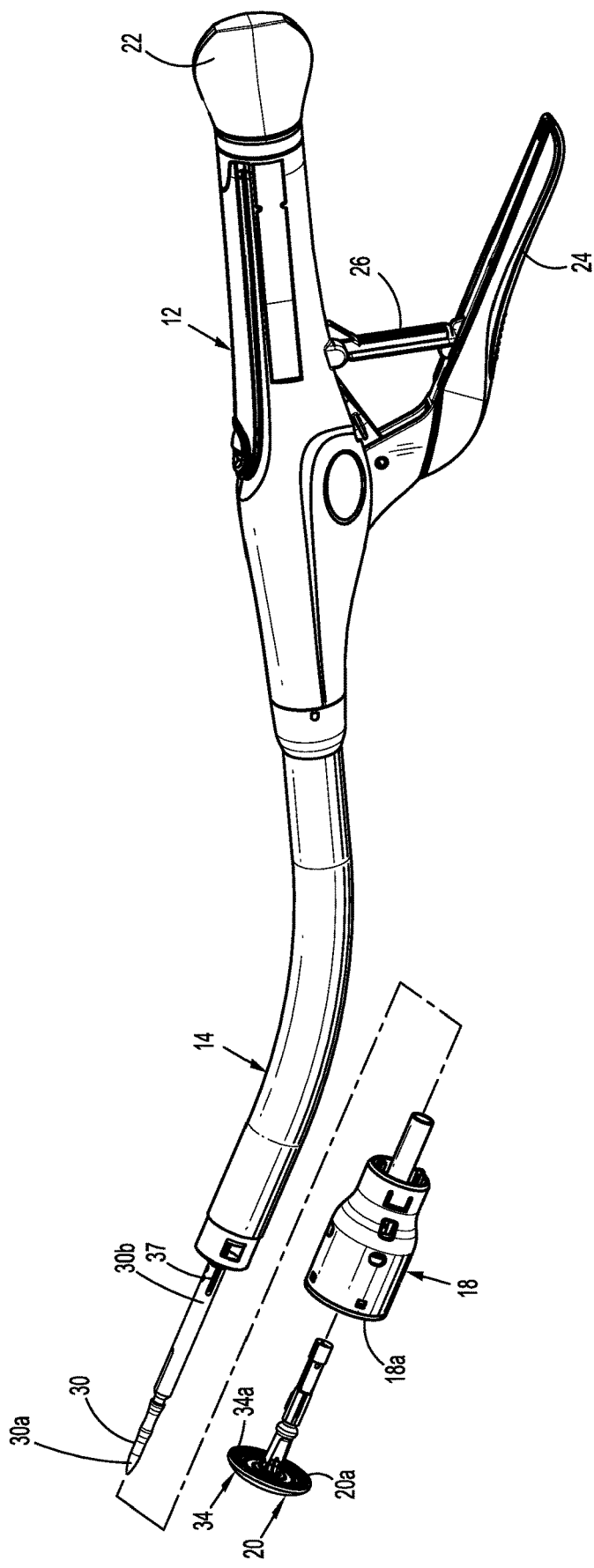
FIG. 2 is a side perspective view of the surgical stapling device shown in FIG. 1 with shell and anvil assemblies of the tool assembly separated from the remaining portion of the stapling device.

Referring to FIGS. 1 and 2, the presently disclosed circular stapling device shown generally as stapling device 10 includes a handle assembly 12, an elongate body portion 14 that extends distally from the handle assembly 12, and a tool assembly 16 that is supported on a distal portion of the elongate body portion 14. The tool assembly 16 includes a shell assembly 18 that supports a staple cartridge 18a and an anvil assembly 20 that includes an anvil head 34 having an anvil surface 34a that defines a plurality of staple deforming recesses 20a (FIG. 2.) The handle assembly 12 includes an approximation knob 22 of an approximation assembly that is operable to move the anvil assembly 20 between unclamped and clamped positions in relation to the cartridge assembly 18, a firing trigger 24 that that operates a firing mechanism (not shown) to fire staples (not shown) from the staple cartridge 18a into tissue, and a firing trigger lockout 26 that is pivotally supported on the handle assembly 12 and is positioned to prevent inadvertent firing of the stapling device 10. For a detailed description of an exemplary circular stapling device including known approximation, firing, and lockout mechanisms, see U.S. Pat. No. 7,857,187 ("the '187 Patent") which is incorporated herein by reference in its entirety.

Although the presently disclosed stapling device 10 is shown and described as being a manually powered device, it is envisioned that the stapling device 10 can also be an electrically powered device such as described in U.S. Patent Publication No. 2015/0048140 which is incorporated herein by reference in its entirety. A surgical stapling component according to any of the embodiments disclosed herein can be configured for use with a robotic surgical stapling system.

The staple cartridge 18a of the shell assembly 18 and the anvil surface 34a (FIG. 2) of the anvil assembly 20 have an annular configuration. The anvil assembly 20 is movable in relation to the shell assembly 18 between a spaced position and a clamped position to move the anvil surface 34a of the anvil head 34 into juxtaposed alignment with the staple cartridge 18a. The staple cartridge 18a defines staple receiving slots 28 (FIG. 1) that are aligned with the staple deforming recesses 20a (FIG. 2) of the anvil surface 34a when the staple cartridge 18a and the anvil surface 34a are properly aligned such that staples ejected from the staple receiving slots 28 are deformed within the staple deforming recesses 20a when the stapling device 10 is fired.

The anvil assembly 20 is releasably supported on an anvil retainer 30 (FIG. 2) of the stapling device 10. The anvil retainer 30 in conjunction with the rotation knob 22 forms part of the approximation mechanism of the stapling device 10 and includes a distal portion 30a and a proximal portion 30b (FIG. 2). The distal portion 30a of the anvil retainer 30 extends from a distal end of the elongate body portion 14 of the stapling device 10 and through the shell assembly 18 to a position to engage the anvil assembly 20. The proximal portion 30b of the anvil retainer 30 is operatively connected to the approximation knob 22 via an approximation linkage 37 (FIG. 2) such that rotation of the approximation knob 22 causes the anvil retainer 30 to move within the shell assembly 18 to move the anvil assembly 20 in relation to the staple cartridge 18a between the spaced position and the clamped position.

The shell assembly 18 includes an annular knife (not shown) that is movable from a retracted position to an advanced position within the shell assembly 18 during firing of the stapling device 10 to transect tissue clamped between the staple cartridge 18a and the anvil surface 34a. (See the '187 Patent.) In some embodiments, the shell assembly 18 is releasably coupled to a distal portion of the elongate body 14 of the stapling device 10 to facilitate replacement of the shell assembly 18 after each firing of the stapling device 10. Mechanisms for releasably coupling the shell assembly 18 to the elongate body portion 14 of the stapling device 10 are described in U.S. Patent Publication Nos. 2016/0310141, 2016/0192938, and 2016/0192934 which are incorporated herein in their entirety by reference. Alternately, the shell assembly 18 can be fixedly secured to the distal portion of the elongate body 14.

Figure 3:
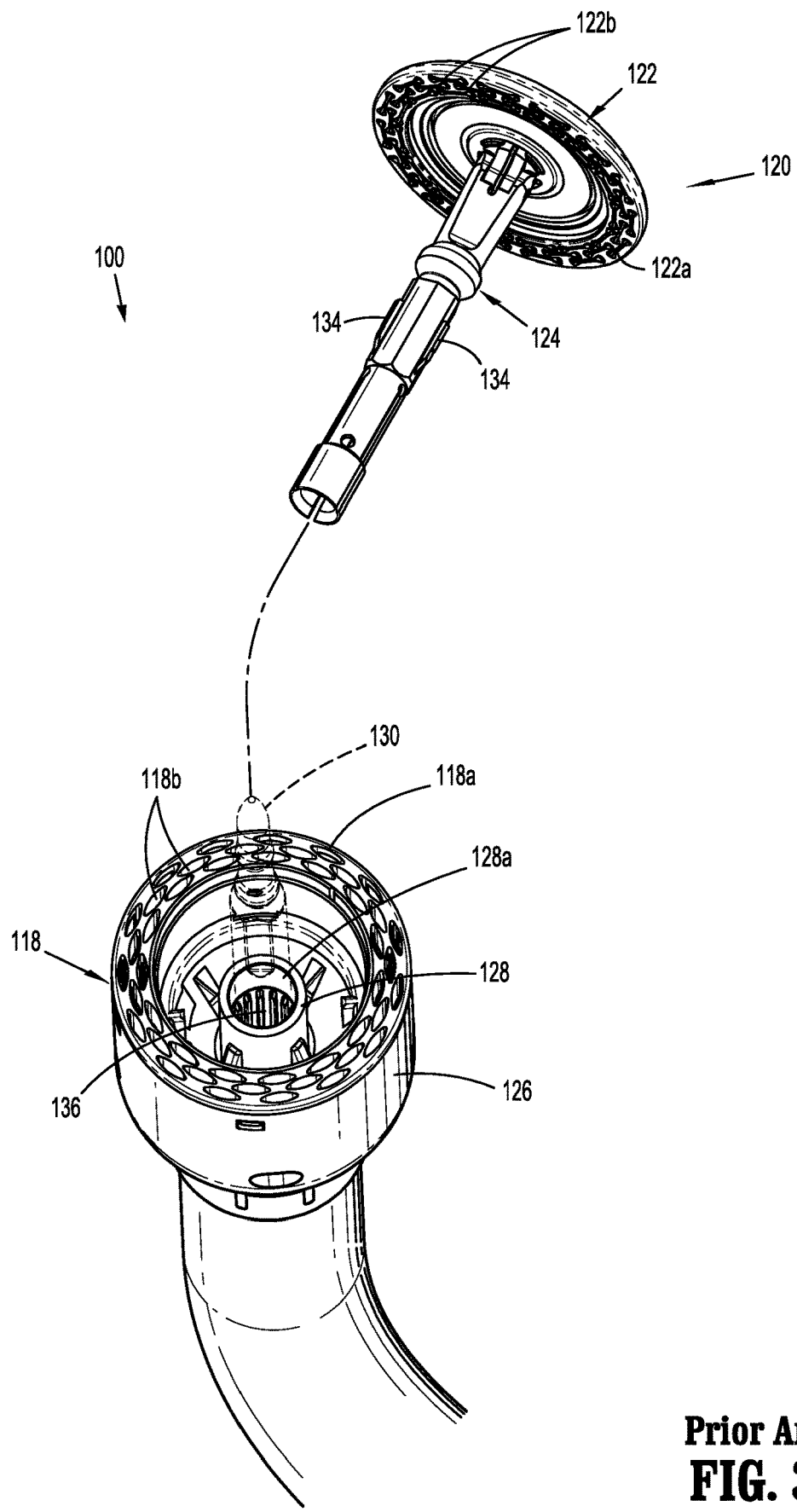
FIG. 3 is a perspective view from a distal end of a "Prior Art" surgical stapling device with the anvil assembly of the tool assembly of the surgical stapling device separated from an anvil retainer (shown in phantom) of the surgical stapling device.

Referring to FIG. 3, prior art circular stapling devices 100 include an anvil assembly 120 having an anvil head 122 and an anvil shaft or center rod 124, and a shell assembly 118 having a staple cartridge 118a and a shell housing 126 having an inner housing portion 128 that defines a through bore 128a. The anvil head 122 defines an anvil surface 122a that defines an annular array of staple deforming recesses 122b and the staple cartridge 118a defines an annular array of staple receiving slots 118b. An anvil retainer 130 (shown in phantom) includes a distal end that is configured to releasably engage the anvil shaft 124 of the anvil assembly 120. The anvil retainer 130 is received within the through bore 128a of the shell housing 126 and is movable between retracted and advanced positions. When the anvil shaft 124 is coupled to the anvil retainer 130 and the anvil retainer 130 is retracted (via actuation of the approximation knob 22, FIG. 1), the anvil shaft 124 is drawn into the through bore 128a of the inner housing portion 128 of the shell housing 126.

The anvil assembly 120 includes splines 134 formed on the anvil shaft 124 and the shell assembly 118 includes splines formed along the inner housing portion 128 of the shell housing 126. In order to align the staple deforming recesses 122b of the anvil surface 122a of the anvil assembly 120 with the staple receiving slots 118b of the staple cartridge 118a of the shell assembly 118, the splines 134 on the anvil shaft 124 including adjacent splines 134a, 134b (FIG. 4) are received in channels 148 defined between the splines 136 formed along an inner wall of the inner housing portion 128 (FIG. 3) of the shell housing 126. Each of the splines 134 of the anvil assembly 120 defines a central axis "Z" and first and second tapered cam surfaces 138a, 138b positioned on opposite sides of the central axis "Z" as viewed in FIG. 4. The tapered surfaces 138a, 138b meet at their proximal ends at an apex 140. Similarly, each of the splines 136 of the shell assembly 118 defines a central axis "X" and first and second tapered cam surfaces 142a, 142b positioned on opposite sides of the central axis "X". The tapered surfaces 142a, 142b meet at their distal ends at an apex 144. As shown, the first and second tapered cam surfaces 138a, 138b have substantially equal surface areas. Similarly, the first and second tapered cam surfaces 142a, 142b of the shell splines 136 have substantially equal surface areas.

When the anvil assembly 120 is attached to the anvil retainer 130 (FIG. 3) and the anvil retainer 130 and anvil assembly 120 are retracted into the through bore 128a (FIG. 3) of the inner housing portion 128 of the shell housing 126, the anvil splines 134 of the anvil assembly 120 move towards the shell splines 136 of the shell assembly 118. If the anvil splines 134 are misaligned with channels 148 defined between the shell splines 136, the apexes 140 of the anvil splines 134a, 134b will engage one of the cam surfaces 142a, 142b of the shell splines 136. When the apexes 140 of the anvil splines 134a, 134b (only two are shown) engage the first tapered cam surface 142a of the splines 136, the engagement urges or cams the anvil assembly 120 to rotate in the direction indicated by arrow "S" (FIG. 4) to realign the anvil splines 134a, 134b so that the anvil splines 134a, 134b enter into the channels 148 defined between the shell splines 136. However, if the apexes 140 of the anvil splines 134a-b are aligned with the apexes 144 of the shell splines 136 such that the apexes 140 and 144 meet head on or "crash", the apexes 140 and 144 may be damaged to that extent that the anvil assembly 120 will not rotate into alignment with the shell assembly 118. When this occurs, alignment between the staple receiving slots 118b of the staple cartridge 118a and the staple deforming recesses 122b of the anvil assembly 120 when the staples are fired. This may result staple malformation.

Figures 4, 5:
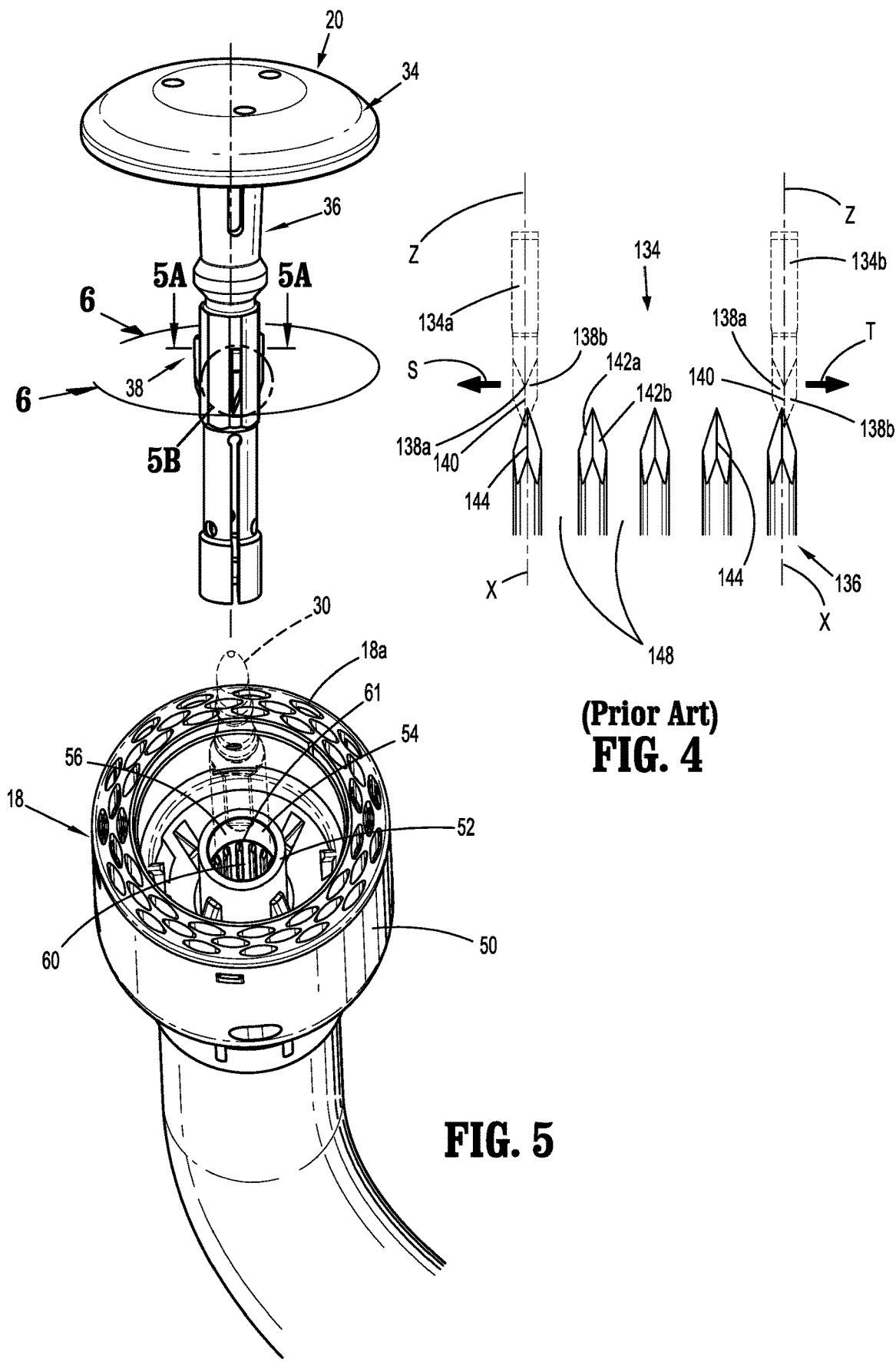
FIG. 4 is a schematic view of a spline configuration of the anvil assembly of the "Prior Art" surgical stapling device shown in FIG. 3.
FIG. 5 is a side perspective view of the anvil assembly of the surgical stapling device shown in FIG. 1.
Figure 5A:
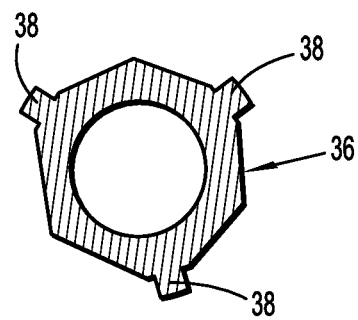
FIG. 5A is a cross-sectional view taken along section line 5A-5A of FIG. 5.
Figure 5B:
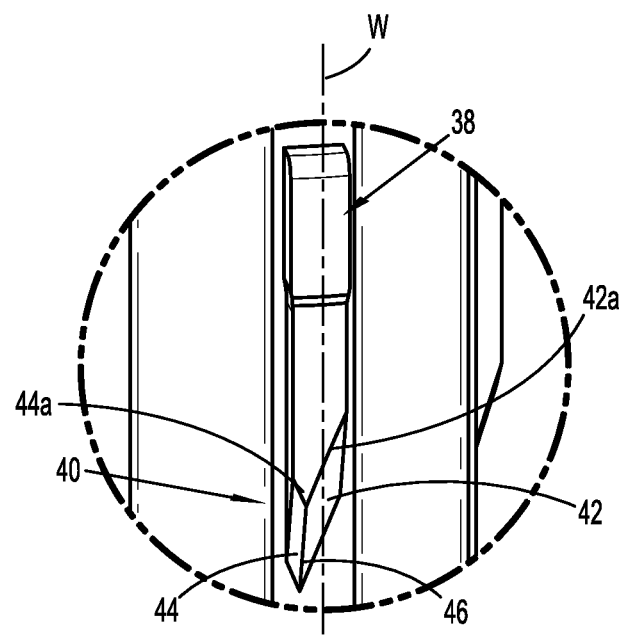
FIG. 5B is an enlarged view of the indicated area of detail shown in FIG. 5.
Figure 6:
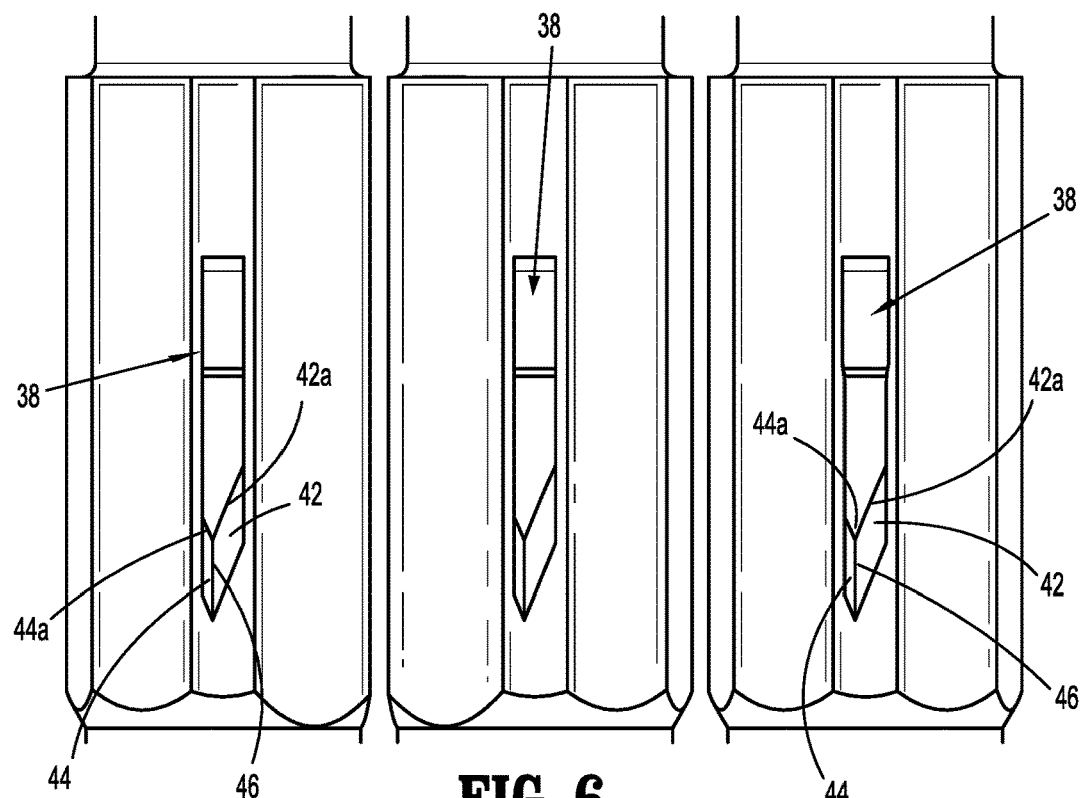
FIG. 6 is a side view taken in the direction indicated by arrows 6-6 of FIG. 5.

Referring to FIGS. 5-6, in the exemplary embodiment of the presently disclosed stapling device 10, the anvil assembly 20 includes the anvil head 34 and an anvil shaft 36. The anvil shaft 36 supports a plurality of splines 38. Each of the splines 38 defines a longitudinal axis "W" and includes a proximally positioned tip 40 that is defined by a first tapered surface 42 and a second tapered surface 44. The first and second tapered surfaces 42, 44 intersect at an apex 46 that is offset to one side of the longitudinal axis "W". The first tapered surface 42 defines a long edge 42a and has a surface area β. The second tapered surface 44 defines a short edge 44a and a second surface area Ω. In embodiments, β is greater than Ω. In some embodiments, β is at least 1.5 times greater than Ω. In other embodiments, β is at least 2 times greater than Ω. In embodiments, the anvil splines 38 are formed from a hard material such as metal.

Referring again to FIG. 5, the shell assembly 18 includes a shell housing 50 having an inner housing portion 52 including an inner wall surface 54 that defines a central bore 56. The central bore 56 is receives the anvil retainer 30 and the anvil shaft 36 of the anvil assembly 20. The inner wall surface 54 of the inner housing portion 52 of the shell housing 50 supports a plurality of shell splines 60. Each of the shell splines 60 defines a guide channel 61 with an adjacent shell spline 60. In embodiments, the shell splines 60 are formed from a polymeric material such as polyethylene.

Figure 7:
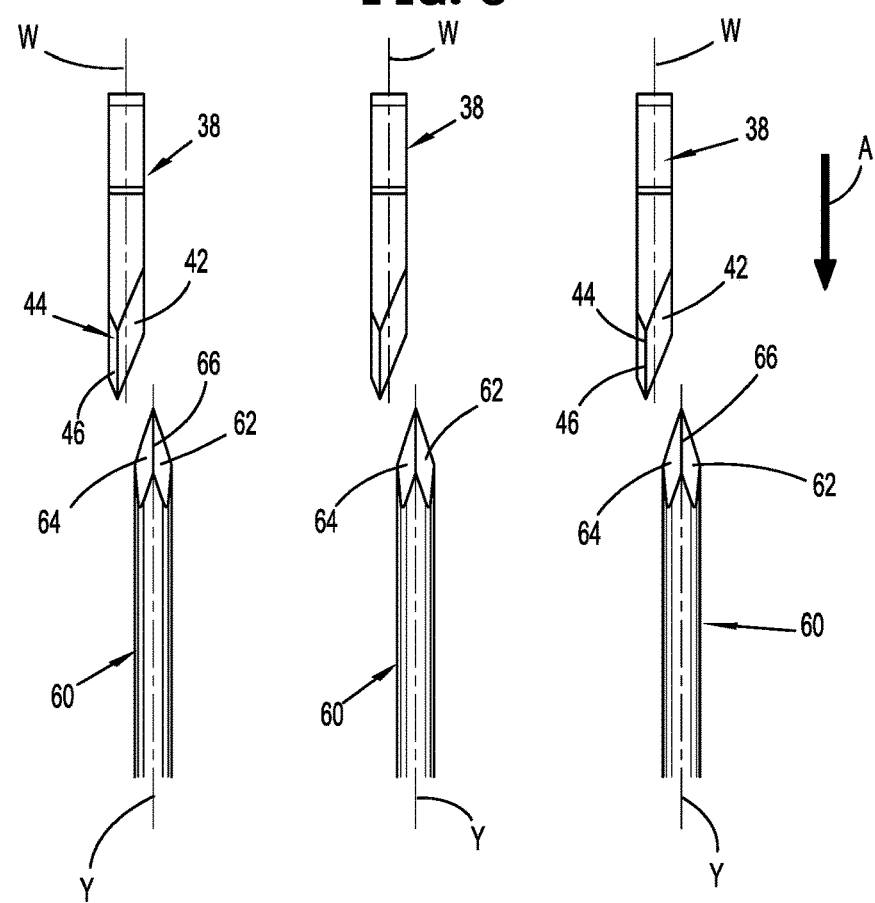
FIG. 7 is a schematic view of the splines of the anvil and cartridge assemblies shown in FIG. 5 in a non-crash condition prior to engagement of the splines of the anvil assembly with the splines of the cartridge assembly.
Figure 8:
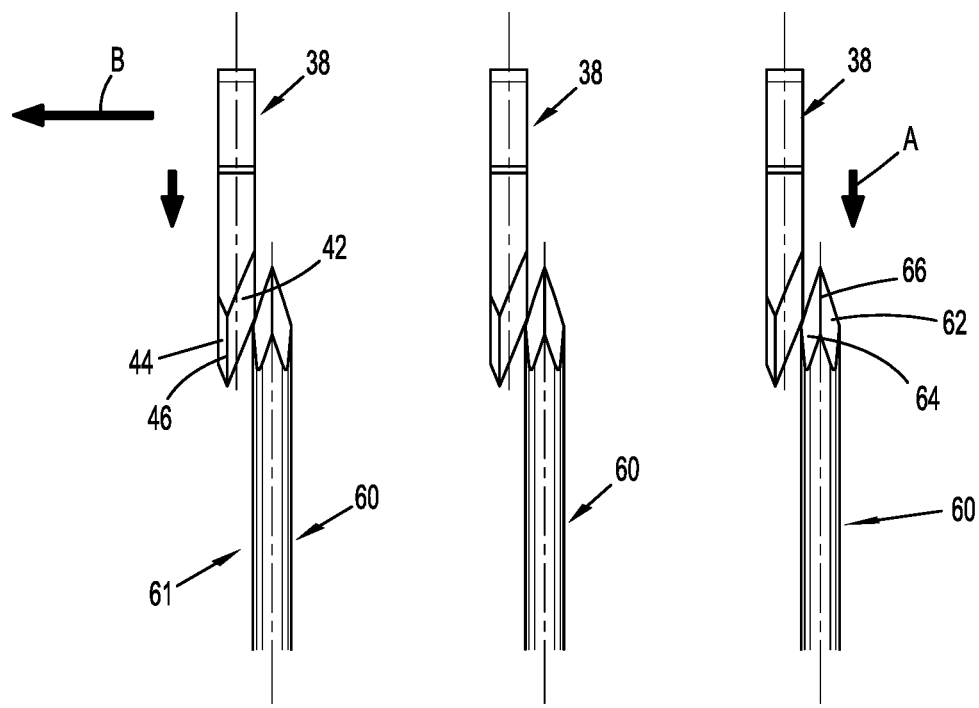
FIG. 8 is a schematic view of the splines of the anvil and cartridge assemblies shown in FIG. 5 in a non-crash condition after engagement of the splines of the anvil assembly with the splines of the cartridge assembly as the splines of the anvil assembly are directed into the guide channels of the shell assembly.
Figure 9:
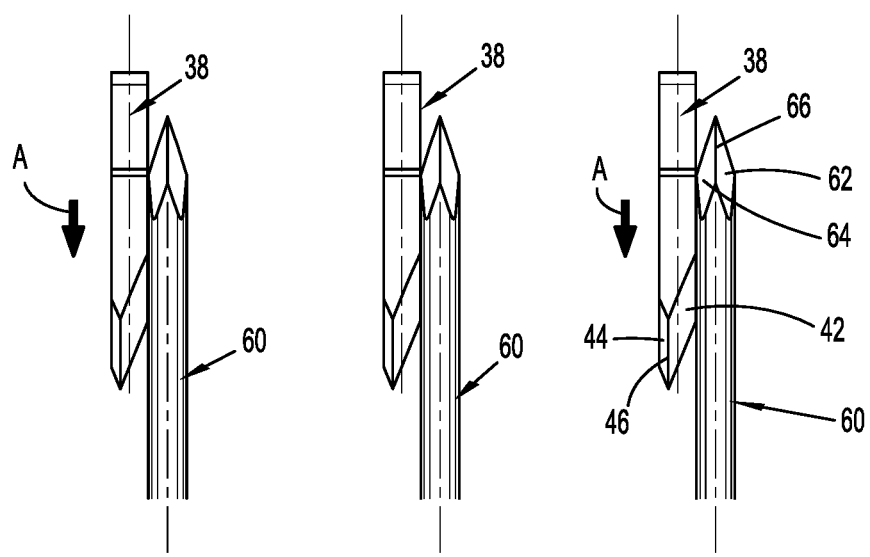
FIG. 9 is a schematic view of the splines of the anvil and cartridge assemblies shown in FIG. 5 in a non-crash condition after engagement of the splines of the anvil assembly with the splines of the cartridge assembly, with the splines of the anvil assembly positioned within the guide channels of the shell assembly.
Figure 10:
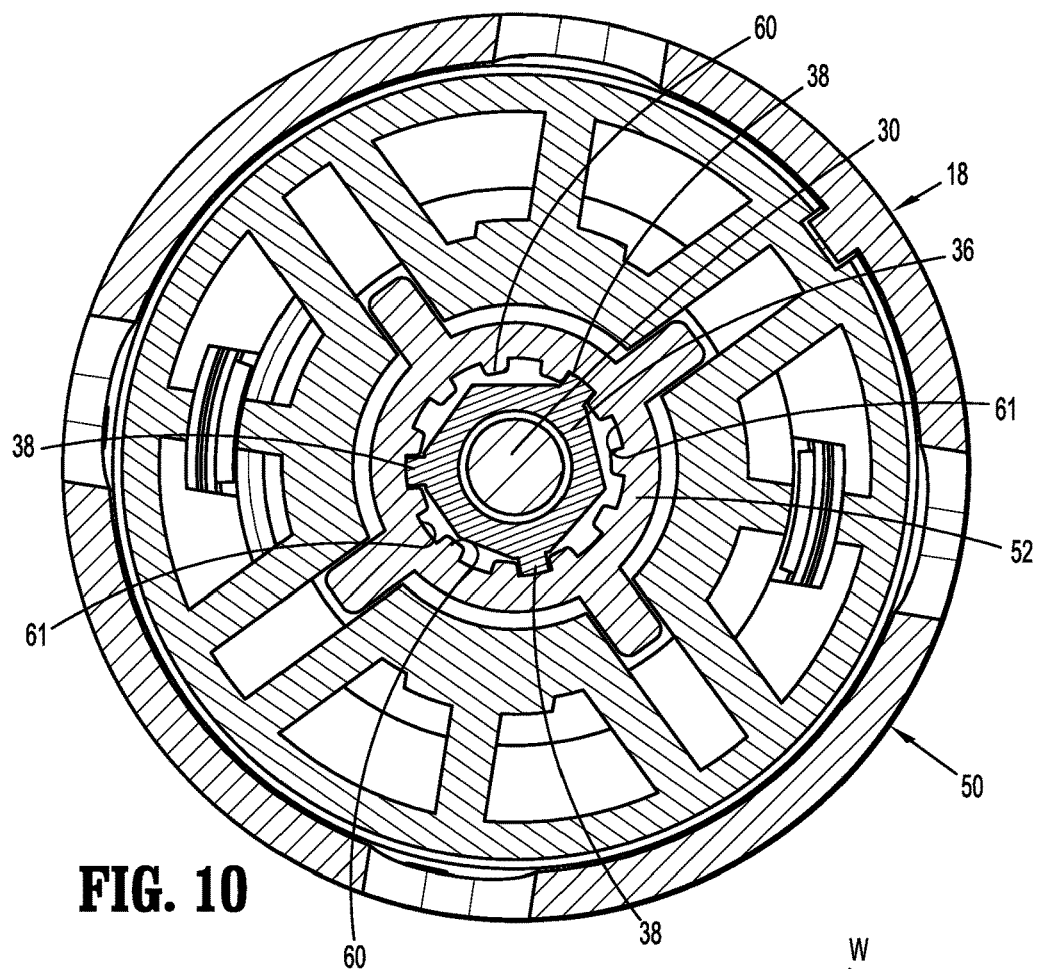
FIG. 10 is a cross-sectional view taken through the splines of the anvil and shell assemblies with the splines of the anvil assembly positioned within the guide channels of the shell assembly as shown in FIG. 9.
Figure 11:
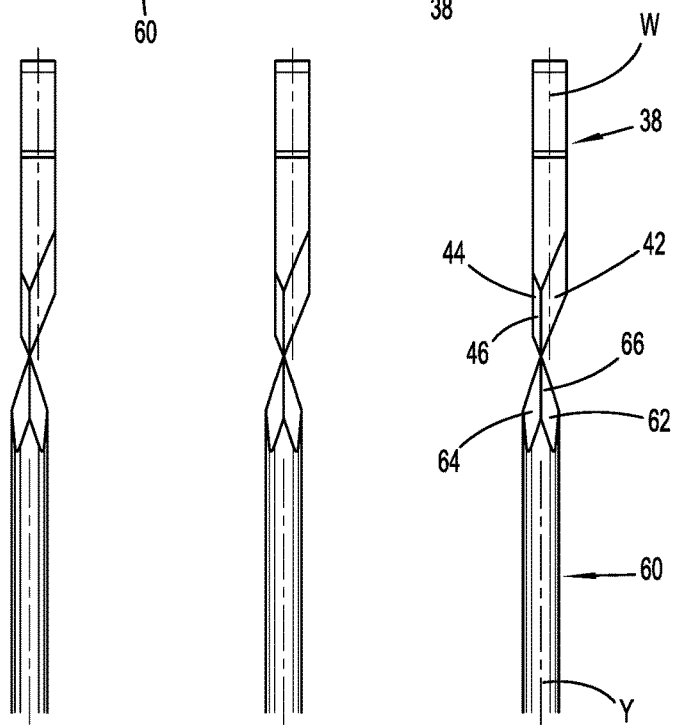
FIG. 11 is a schematic view of the splines of the anvil and cartridge assemblies shown in FIG. 5 in a crash condition as the apex of the splines of the anvil assembly initially engage the splines of the cartridge assembly.

Referring to FIG. 7, each of the shell splines 60 defines a longitudinal axis "Y" and includes first and second tapered cam surfaces 62 and 64. The first and second tapered cam surfaces 62 and 64 intersect at an apex 66 that is aligned with the longitudinal axis "Y" of the spline 60 such that the area of the first cam surface 62 is substantially equal to the area of the second cam surface 64.

Referring to FIGS. 7-10, when the anvil assembly 20 is secured to the anvil retainer 30 (FIG. 10) and the anvil retainer 30 and the anvil shaft 36 (FIG. 10) of the anvil assembly 20 are withdrawn into the central bore 56 of the inner housing portion 52 of the shell housing 50 (FIG. 10) in the direction indicated by arrow "A" in FIG. 7, the anvil splines 38 are moved towards and into engagement with the shell splines 60. When the apex 46 of each of the anvil splines 38 is offset from the apex 66 of the respective shell splines 60 such that the apex 46 of the anvil splines 38 engage one of the right or left tapered surfaces 62, 64 of the shell splines 60, the anvil assembly 20 (FIG. 1) is cammed in either a clockwise or counterclockwise direction to guide the anvil splines 38 into one of the guide channels 61 (FIG. 10) positioned between the shell splines 60. For example, when the apex 46 of the anvil splines 38 engage one of the left tapered surfaces 62, 64 of the respective shell splines 60, the anvil assembly 20 is cammed in the direction indicated by arrow "B" in FIG. 8 to direct the anvil splines 38 into the guide channels 61 (FIG. 10) positioned between adjacent shell splines 60. This movement properly aligns the anvil assembly 20 in relation to the shell assembly 18 for firing of the stapling device 10.

Figure 12:
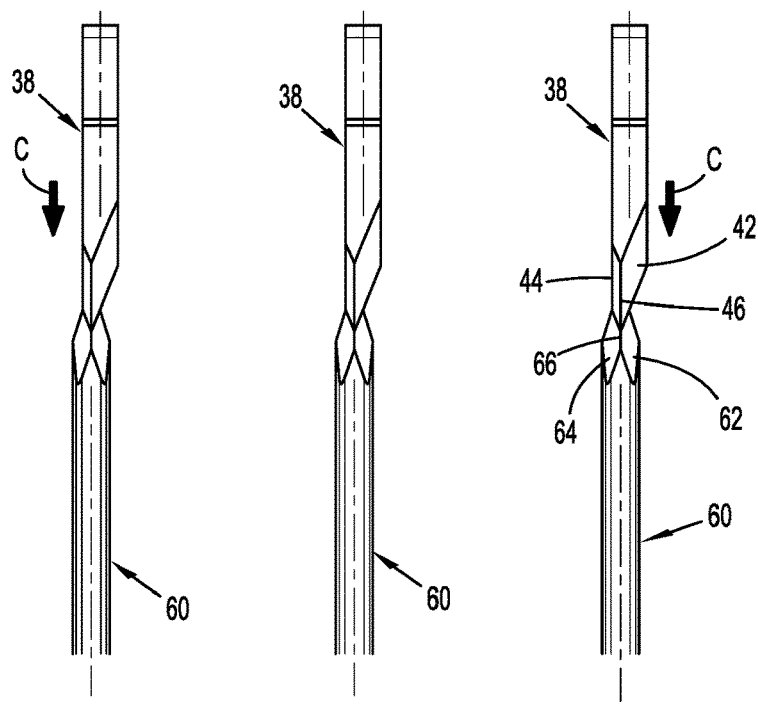
FIG. 12 is a schematic view of the splines of the anvil and cartridge assemblies shown in FIG. 5 in a crash condition as the apex of the splines of the anvil assembly crash into the splines of the cartridge assembly.

Referring to FIGS. 11-16, when the anvil assembly 20 is secured to the anvil retainer 30 (FIG. 15) and the anvil retainer 30 and the anvil shaft 36 of the anvil assembly 20 are withdrawn into the central bore 56 of the inner housing portion 52 of the shell housing 50 (FIG. 15) in the direction indicated by arrow "C" in FIG. 12, the anvil splines 38 are moved towards and into engagement with the shell splines 60. When the apex 46 of each of the anvil splines 38 is aligned with a respective apex 66 of the shell splines 60, the apex 46 of each of the anvil splines 38 crashes into the apex 66 of the shell splines 60. When the apex 46 of the metal anvil splines 38 engage the polymeric shell splines 60 and the anvil shaft 36 is withdrawn further into the central bore 56 of the inner housing portion 52 of the shell housing 50, the anvil splines 38 migrate or penetrate into the shell splines 60 (FIG. 12).

Figure 13:
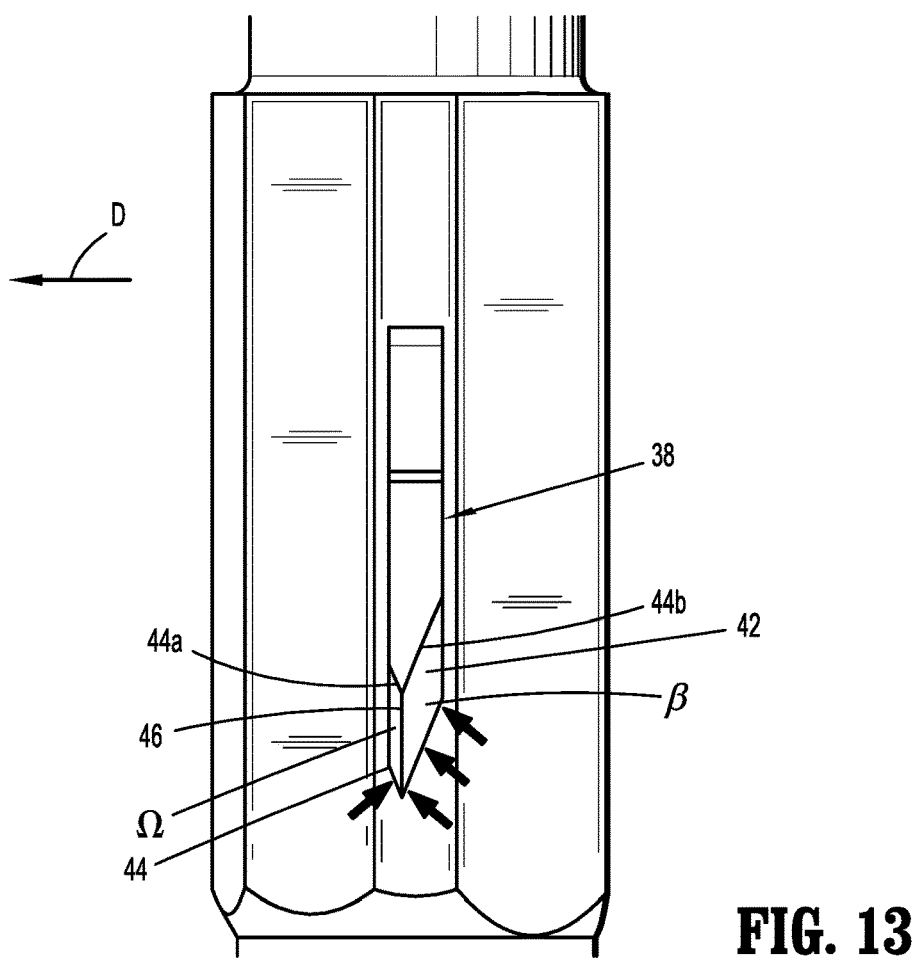
FIG. 13 is a side view of one of the splines of the anvil assembly shown in FIG. 5 illustrating the crash forces applied to the anvil spline as the anvil spline crashes into one of the splines of the shell assembly.
Figure 14:
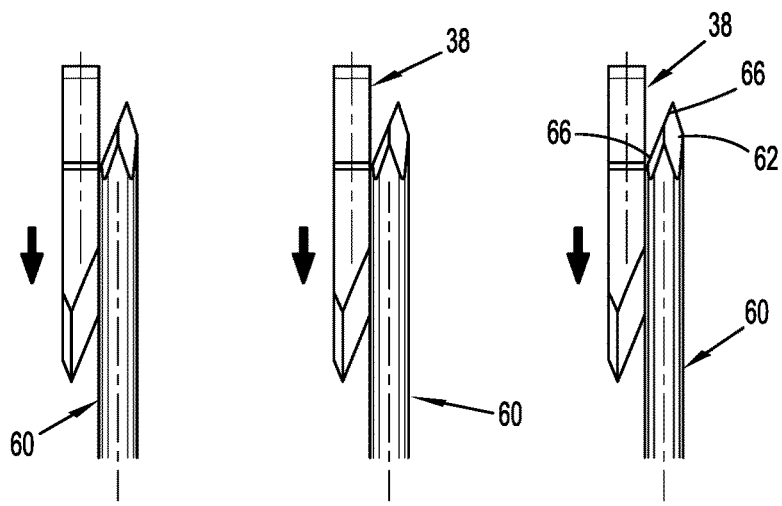
FIG. 14 is a schematic view of the splines of the anvil and cartridge assemblies shown in FIG. 5 after engagement of the splines of the anvil assembly with the splines of the cartridge assembly, with the splines of the anvil assembly positioned within the guide channels of the shell assembly.
Figure 15:
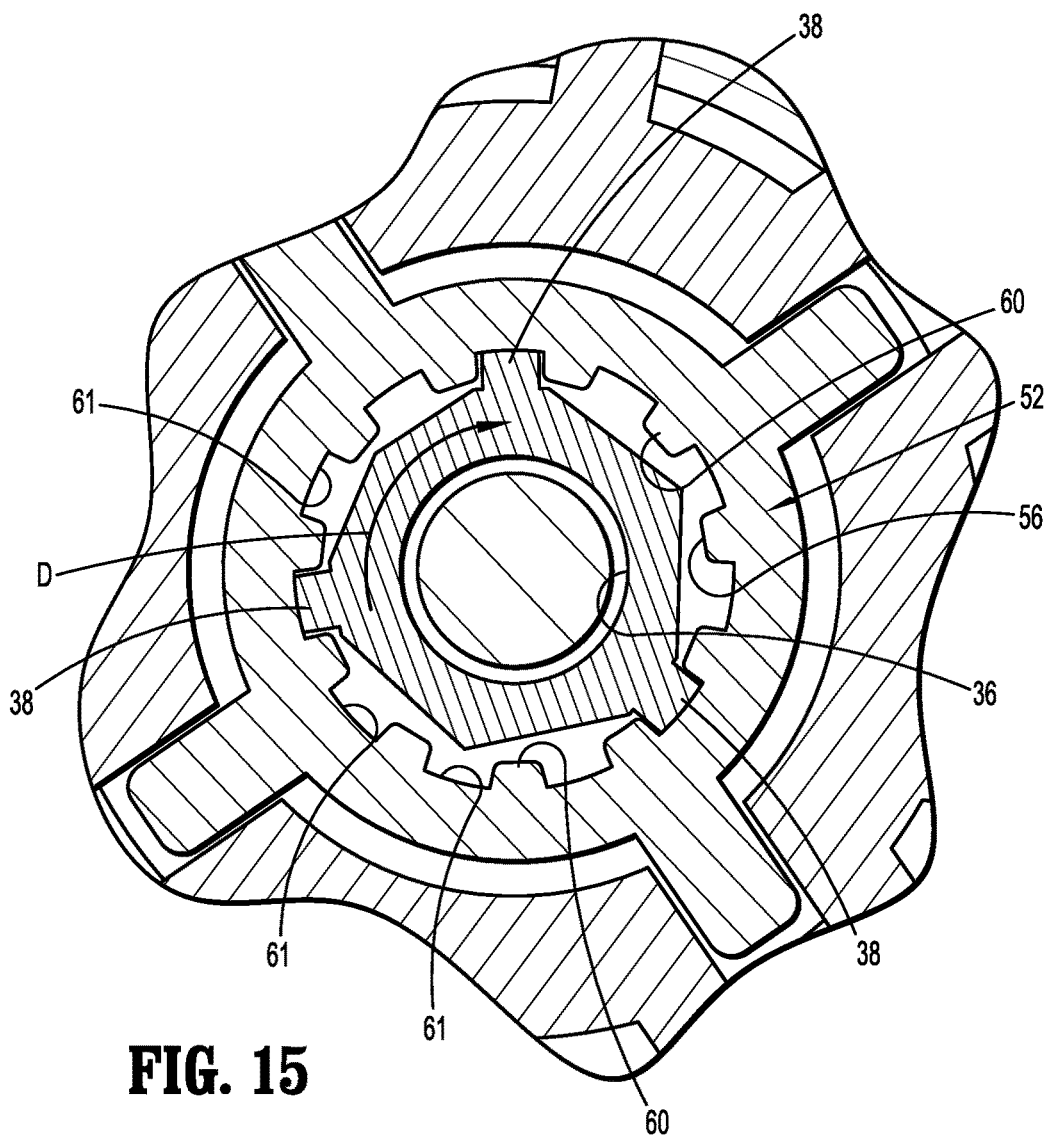
FIG. 15 is a cross-sectional view taken through the splines of the anvil and shell assemblies shown in FIG. 5 with the splines of the anvil assembly positioned within the guide channels of the shell assembly as shown in FIG. 14.
Figure 16:
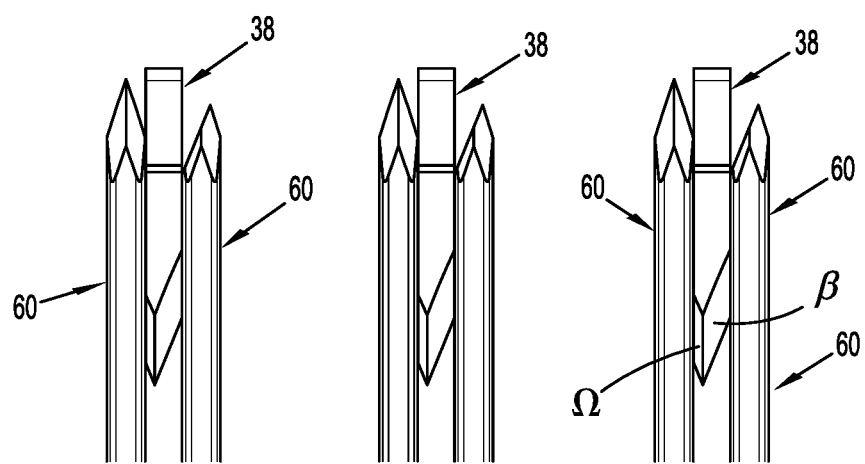
FIG. 16 is a schematic view of the splines of the anvil and cartridge assemblies shown in FIG. 5 after engagement of the splines of the anvil assembly with the splines of the cartridge assembly, with the splines of the anvil assembly positioned within the guide channels of the shell assembly.

As shown in FIG. 13, as the anvil splines 38 migrate into the shell splines 60, the forces applied by the tapered surface 42 defined by the long edge and having the greater surface area β applies a higher force on one side of the shell spline 60 to cam or urge the anvil assembly 20 (FIG. 1) into rotation in the direction indicated by arrow "D" in FIG. 15. As the anvil assembly 18 rotates in relation to the shell assembly 18, the anvil splines 38 break through the respective shell splines 60 and are directed into the guide channels 61 positioned between the shell splines 60 of the shell assembly 20 (FIG. 16). The short edge 44a and a second surface area Ω of the left tapered surface 44 engage an adjacent shell spline 60a (FIG. 16) to prevent the anvil splines 38 from migrating into the adjacent shell splines.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
an approximation assembly including an anvil retainer;
a shell assembly including a staple cartridge and a shell housing, the shell housing having an inner housing portion defining a bore, a plurality of shell splines supported on the inner housing portion within the bore, each of the plurality of shell splines defining a guide channel with an adjacent one of the plurality of shell splines, the staple cartridge being supported on the shell housing; and
an anvil assembly including an anvil shaft having at least one anvil spline and an anvil head having an anvil surface defining a plurality of staple deforming recesses, the at least one anvil spline defining a longitudinal axis, the anvil shaft being configured to releasably engage the anvil retainer and the anvil head being supported on a distal portion of the anvil shaft, wherein the at least one anvil spline includes first and second tapered surfaces that intersect at an apex that is offset to one side of the longitudinal axis, the first tapered surface having a surface area β and the second tapered surface having a surface area Ω that is different from surface area β.

2. The surgical stapling device of claim 1, wherein β is at least 1.5 times greater than Ω.

3. The surgical stapling device of claim 1, wherein β is at least 2 times greater than Ω.

4. The surgical stapling device of claim 1, wherein the at least one anvil spline is formed from metal and the plurality of shell splines is formed from a polymer.

5. The surgical stapling device of claim 1, wherein each of the plurality of shell splines defines a longitudinal axis and includes first and second tapered cam surfaces, the first and second tapered cam surfaces of each of the plurality of shell splines intersecting at an apex.

6. The surgical stapling device of claim 5, wherein the apex of each of the plurality of shell splines is aligned with the longitudinal axis of the shell spline.

7. The surgical stapling device of claim 6, wherein the first cam surface of each of the plurality of shell splines has a surface area that is equal to a surface area of the second cam surface of each of the plurality of shell splines.

8. The surgical stapling device of claim 1, wherein at least one the anvil spline is formed to migrate into a respective shell spline of the plurality of the shell splines when the apex of the at least one anvil spline engages the apex of a respective one of the plurality of shell splines.

9. An anvil assembly for a circular stapling device comprising:
an anvil shaft having at least one anvil spline and an anvil head having an anvil surface defining a plurality of staple deforming recesses, the at least one anvil spline defining a longitudinal axis, the anvil head being supported on a distal portion of the anvil shaft, wherein the at least one anvil spline includes first and second tapered surfaces that intersect at an apex that is offset to one side of the longitudinal axis, the first tapered surface having a surface area β and the second tapered surface having a surface area Ω that is different from surface area β.

10. The anvil assembly of claim 9, wherein β is at least 1.5 times greater than Ω.

11. The anvil assembly of claim 9, wherein β is at least 2 times greater than Ω.

12. The anvil assembly of claim 9, wherein the at least one anvil spline is formed from metal.

13. A tool assembly comprising:
a shell assembly including a staple cartridge and a shell housing, the shell housing having an inner housing portion defining a bore, a plurality of shell splines supported on the inner housing portion within the bore, each of the plurality of shell splines defining a guide channel with an adjacent one of the plurality of shell splines, the staple cartridge being supported on the shell housing; and
an anvil assembly including an anvil shaft having at least one anvil spline and an anvil head having an anvil surface defining a plurality of staple deforming recesses, the at least one anvil spline defining a longitudinal axis, the anvil head being supported on a distal portion of the anvil shaft, wherein the at least one anvil spline includes first and second tapered surfaces that intersect at an apex that is offset to one side of the longitudinal axis, the first tapered surface having a surface area β and the second tapered surface having a surface area Ω that is different from surface area β.

14. The surgical stapling device of claim 13, wherein β is at least 1.5 times greater than Ω.

15. The surgical stapling device of claim 14, wherein β is at least 2 times greater than Ω.

16. The surgical stapling device of claim 13, wherein the at least one anvil spline is formed from metal and the plurality of shell splines is formed from a polymer.

17. The surgical stapling device of claim 13, wherein each of the plurality of shell splines defines a longitudinal axis and includes first and second tapered cam surfaces, the first and second tapered cam surfaces of each of the plurality of shell splines intersecting at an apex.

18. The surgical stapling device of claim 17, wherein the apex of each of the plurality of shell splines is aligned with the longitudinal axis of the shell spline.

19. The surgical stapling device of claim 18, wherein the first cam surface of each of the plurality of shell splines has a surface area that is equal to a surface area of the second cam surface of each of the plurality of shell splines.

20. The surgical stapling device of claim 13, wherein at least one the anvil spline is formed to migrate into a respective shell spline of the plurality of the shell splines when the apex of the at least one anvil spline engages the apex of a respective one of the plurality of shell splines.

* * * * *